(12) United States Patent
Xu

(10) Patent No.: US 11,960,640 B2
(45) Date of Patent: Apr. 16, 2024

(54) DISPLAY METHOD AND DISPLAY DEVICE FOR INTERACTIVE INTERFACE AND STORAGE MEDIUM

(71) Applicant: BOE Technology Group Co., Ltd., Beijing (CN)

(72) Inventor: Zhihong Xu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 21 days.

(21) Appl. No.: 17/773,371

(22) PCT Filed: Jun. 8, 2021

(86) PCT No.: PCT/CN2021/098954
§ 371 (c)(1),
(2) Date: Apr. 29, 2022

(87) PCT Pub. No.: WO2022/022077
PCT Pub. Date: Feb. 3, 2022

(65) Prior Publication Data
US 2022/0404906 A1 Dec. 22, 2022

(30) Foreign Application Priority Data
Jul. 29, 2020 (CN) .......................... 202010743658.7

(51) Int. Cl.
*G06F 3/01* (2006.01)
*G06F 3/0484* (2022.01)
*G06V 40/16* (2022.01)

(52) U.S. Cl.
CPC ............ *G06F 3/012* (2013.01); *G06F 3/0484* (2013.01); *G06V 40/161* (2022.01); *G06V 40/176* (2022.01); *G06V 40/178* (2022.01)

(58) Field of Classification Search
CPC ...... G06F 3/012; G06F 3/0484; G06F 3/0481; G06F 3/0488; G06F 3/011; G06F 2203/011; G06F 9/451; G06V 40/161; G06V 40/176; G06V 40/178; G06V 40/174; G10L 25/63; G16H 20/70
See application file for complete search history.

(56) References Cited

U.S. PATENT DOCUMENTS

2017/0162072 A1 * 6/2017 Horseman ............ A61B 5/6803
2020/0110927 A1   4/2020 Shaffer
(Continued)

FOREIGN PATENT DOCUMENTS

CN   103186327 A   7/2013
CN   104063147 A   9/2014
(Continued)

*Primary Examiner* — Phuong H Nguyen
(74) *Attorney, Agent, or Firm* — WHDA, LLP

(57) ABSTRACT

The present disclosure provides a display method and a display device for an interactive interface and a computer-readable storage medium. The display method for the interactive interface includes: determining, from at least one object, a target object to interact through the interactive interface; acquiring an attribute information of the target object and an emotion information of the target object; and controlling a display of a first object region of the interactive interface according to the attribute information of the target object and the emotion information of the target object.

15 Claims, 5 Drawing Sheets

100

```
┌─────────────────────────────────────────────────┐         S210
│ A target object to interact through the          │────────/
│ interactive interface is determined from at      │
│ least one object                                 │
└─────────────────────────────────────────────────┘
                        │
                        ▼
┌─────────────────────────────────────────────────┐         S220
│ An attribute information of the target object    │────────/
│ and an emotion information of the target object  │
│ are acquired                                     │
└─────────────────────────────────────────────────┘
                        │
                        ▼
┌─────────────────────────────────────────────────┐         S230
│ A display of a first object region of the        │────────/
│ interactive interface is controlled according    │
│ to the attribute information of the target       │
│ object and the emotion information of the        │
│ target object                                    │
└─────────────────────────────────────────────────┘
```

(56) References Cited

U.S. PATENT DOCUMENTS

| | | | | |
|---|---|---|---|---|
| 2020/0151471 A1* | 5/2020 | Han | ........................ | G06F 3/167 |
| 2020/0226388 A1* | 7/2020 | Ghessassi | ............ | G06V 40/174 |
| 2021/0223869 A1* | 7/2021 | Heraz | ............... | G06F 18/24323 |
| 2022/0021742 A1* | 1/2022 | Zhang | ................... | G06F 16/436 |

FOREIGN PATENT DOCUMENTS

| | | |
|---|---|---|
| CN | 105955490 A | 9/2016 |
| CN | 110070879 A | 7/2019 |
| CN | 111326235 A | 6/2020 |

* cited by examiner

DISPLAY METHOD AND DISPLAY DEVICE FOR INTERACTIVE INTERFACE AND STORAGE MEDIUM

CROSS REFERENCE TO RELATED APPLICATION(S)

This application is a national phase of PCT application No. PCT/CN2021/098954, which claims priority to Chinese patent Application No. 202010743658.7 filed on Jul. 29, 2020, the content of which are incorporated herein by reference in their entirety.

TECHNICAL FIELD

The present disclosure relates to a field of human-computer interaction, in particular to a display method and a display device for an interactive interface, and a computer-readable storage medium.

BACKGROUND

A rapid development of AI (Artificial Intelligence) technology has promoted an application of human-computer interaction products. At present, a human-computer interaction product capable of monitoring and managing a human emotion has been applied in a field of health care. Such a human-computer interaction product may replace or assist medical personnel to assess a patient's mental state for further treatment. However, a result of record may be inaccurate due to patient resistance to the interaction product.

SUMMARY

A first aspect of the embodiments of the present disclosure provides a display method for an interactive interface, including: determining, from at least one object, a target object to interact through the interactive interface; acquiring an attribute information of the target object and an emotion information of the target object; and controlling a display of a first object region of the interactive interface according to the attribute information of the target object and the emotion information of the target object.

According to the embodiments, the determining, from at least one object, a target object to interact through the interactive interface includes: tracking and detecting the at least one object to acquire an image about the at least one object; identifying the image to acquire a face information of the at least one object in the image; and determining, according to the face information of the at least one object, an object appearing for a first time in the image or an object located at the front of the at least one object in the image as the target object to interact through the interactive interface.

According to the embodiments, the attribute information contains an age and a gender, and the acquiring an attribute information of the target object includes: acquiring the age of the target object by using an age estimation algorithm according to a face information of the target object in the face information of the at least one object; and acquiring the gender of the target object by using a gender estimation algorithm according to the face information of the target object in the face information of the at least one object.

According to the embodiments, the emotion information contains an emotion value, and the acquiring an emotion information of the target object includes: acquiring the emotion value of the target object by using an emotion recognition algorithm according to the face information of the target object in the face information of the at least one object.

According to the embodiments, the controlling a display of a first object region of the interactive interface according to the attribute information of the target object and the emotion information of the target object includes: determining a display image for the target object in the first object region of the interactive interface according to the attribute information of the target object; and varying the display image in the first object region according to the emotion information of the target object.

According to the embodiments, the emotion information contains an emotion value, and the varying the display image in the first object region according to the emotion information of the target object includes: determining an emotional characteristic value of the target object according to the emotion value of the target object; displaying the display image in a first display mode as the emotion characteristic value decreases, in response to the emotion characteristic value being less than a first emotion threshold; maintaining the display image in response to the emotional characteristic value being greater than or equal to the first emotion threshold and less than or equal to a second emotion threshold; and displaying the display image in a second display mode as the emotional characteristic value increases, in response to the emotional characteristic value being greater than the second emotion threshold.

According to the embodiments, the display method for the interactive interface further includes: acquiring an emotion information of each of the at least one object; and controlling a display of a second object region of the interactive interface according to the emotion information of each of the at least one object.

According to the embodiments, the emotion information contains an emotion value, and the controlling a display of a second object region of the interactive interface according to the emotion information of each of the at least one object includes: determining an emotional characteristic value of each of the at least one object according to the emotion value of each of the at least one object; acquiring an average value of the emotional characteristic value according to the emotional characteristic value of each of the at least one object; displaying a background pattern in the second object region in a third mode as the average value of the emotional characteristic value decreases, in response to the average value of the emotional characteristic value being less than a first average emotion value threshold; maintaining the background pattern in the second object region in response to the average value of the emotional characteristic value being greater than or equal to the first average emotion value threshold and less than or equal to a second average emotion value threshold; and displaying the background pattern in the second object region in a fourth mode as the average value of the emotional characteristic value increases, in response to the average value of the emotional characteristic value being greater than the second average emotion value threshold.

According to the embodiments, the emotion recognition algorithm includes one of a K-nearest neighbor algorithm, a support vector machine algorithm, a clustering algorithm, a genetic algorithm, a particle swarm optimization algorithm, a convolutional neural network algorithm and a multi-task convolutional neural network algorithm.

A second aspect of the embodiments of the present disclosure provides a display device for an interactive interface, including: a memory configured to store program instructions; and a processor configured to execute the program instructions to: determine, from at least one object, a target object to interact through the interactive interface; acquire an attribute information of the target object and an emotion information of the target object; and control a display of a first object region of the interactive interface according to the attribute information of the target object and the emotion information of the target object.

According to the embodiments, the processor is further configured to: acquire an emotion information of each of the at least one object; and control a display of a second object region of the interactive interface according to the emotion information of each of the at least one object.

A third aspect of the embodiments of the present disclosure provides a computer-readable storage medium having executable instructions stored thereon, wherein the instructions, when executed by a processor, cause the processor to perform the display method for the interactive interface provided according to the first aspect of the embodiments of the present disclosure.

BRIEF DESCRIPTION OF THE DRAWINGS

The above and other objectives, features and advantages of the present disclosure will be more apparent through the following description of embodiments of the present disclosure with reference to the accompanying drawings.

Throughout the drawings, the same reference numerals refer to the same elements.

DETAILED DESCRIPTION OF EMBODIMENTS

Embodiments of the present disclosure will be described below with reference to the accompanying drawings. It should be understood, however, that these descriptions are merely exemplary and are not intended to limit the scope of the present disclosure. In the following detailed description, for ease of interpretation, many specific details are set forth to provide a comprehensive understanding of the embodiments of the present disclosure. However, it is clear that one or more embodiments may also be implemented without these specific details. In addition, in the following description, descriptions of well-known structures and technologies are omitted to avoid unnecessarily obscuring the concepts of the present disclosure.

The terms used herein are for the purpose of describing specific embodiments only and are not intended to limit the present disclosure. The terms "including", "containing" and the like used herein indicate the presence of the feature, step, operation and/or part, but do not exclude the presence or addition of one or more other features, steps, operations or parts.

All terms used herein (including technical and scientific terms) have the meanings generally understood by those skilled in the art, unless otherwise defined. It should be noted that the terms used herein shall be interpreted to have meanings consistent with the context of this specification, and shall not be interpreted in an idealized or too rigid way.

In a case of using the expression similar to "at least one of A, B and C", it should be explained according to the meaning of the expression generally understood by those skilled in the art (for example, "a system including at least one of A, B and C" should include but not be limited to a system including only A, a system including only B, a system including only C, a system including A and B, a system including A and C, a system including B and C, and/or a system including A, B and C).

An interactive interface according to the embodiments of the present disclosure may be provided and applied in a human-computer interaction system capable of monitoring or managing a human emotion, which may acquire an emotional state information of a target object and assess and treat an emotional state of the target object. The above-mentioned human-computer interaction system will be illustrated by way of example in describing the interactive interface in the following embodiments. However, those skilled in the art should understand that the interactive interface, a display method for the interactive interface and a display device for the interactive interface in the embodiments of the present disclosure are not limited to this and may be applied to any other suitable product or application scenario.

Figure 1:
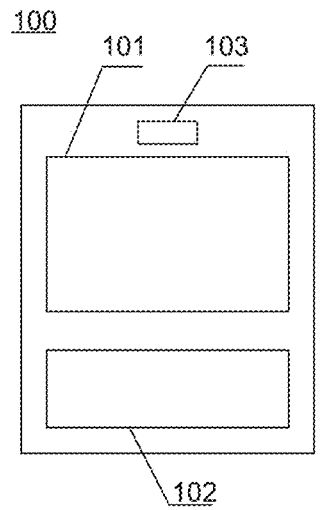
FIG. 1 shows a schematic diagram of a human-computer interaction system provided with an interactive interface according to the embodiments of the present disclosure.
Figure 2:
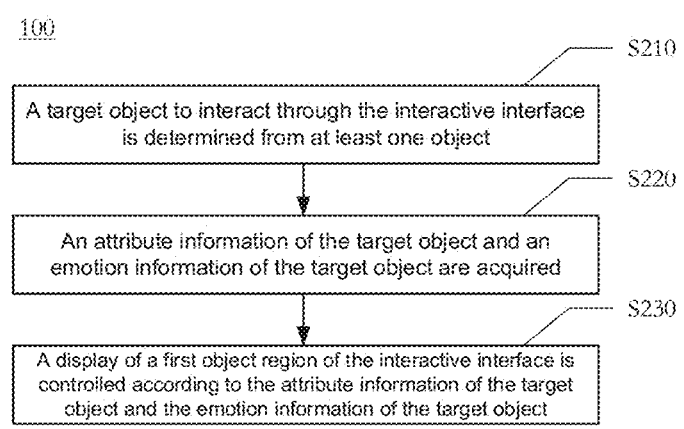
FIG. 2 shows a flowchart of a display method for an interactive interface according to the embodiments of the present disclosure.

FIG. 1 shows a schematic diagram of a human-computer interaction system provided with an interactive interface according to the embodiments of the present disclosure. FIG. 2 shows a flowchart of a display method for an interactive interface according to the embodiments of the present disclosure.

As shown in FIG. 1, a human-computer interaction system 100 includes an interactive interface 101 and a functional region 102. The interactive interface 101 may provide a screen display to a user based on a display technology, and the functional region 102 may receive a user input and operate the human-computer interaction system 100 according to the user input, such as turning on or off the human-computer interaction system 100, setting a parameter of the human-computer interaction system 100, or selecting a function of the human-computer interaction system 100, etc. As shown in FIG. 1, the human-computer interaction system 100 further includes an image sensor 103 that may be configured to capture an object so as to provide the interactive interface 101 with an image containing the object, so that the interactive interface 101 may select an object to interact through the interactive interface 101 by identifying the image.

It should be noted that the human-computer interaction system 100 in FIG. 1 is only an example, and does not constitute a limitation on the human-computer interaction system 100 and the interactive interface 101 provided in the human-computer interaction system 100. For example, the human-computer interaction system 100 may be implemented by a mobile terminal such as a smart phone and an application installed on the mobile terminal. A function of the interactive interface 101 may be achieved by, for example, a screen of the smart phone, a function of the functional region 102 may be achieved by an operation of the application, and a function of the image sensor 103 may be achieved by a camera of the smart phone.

As shown in FIG. 2, a display method 200 for an interactive interface according to the embodiments of the present disclosure includes the following steps.

In step S210, a target object to interact through the interactive interface is determined from at least one object.

In step S220, an attribute information of the target object and an emotion information of the target object are acquired.

In step S230, a display of a first object region of the interactive interface is controlled according to the attribute information of the target object and the emotion information of the target object.

Specifically, in step S210, the display method 200 may be implemented to determine the target object to interact through the interactive interface in a scene where a plurality of objects exist. The method of determining the target object from the at least one object may include: tracking and detecting the at least one object to acquire an image about the at least one object, identifying the image to acquire a face information of the at least one object in the image, and determining, according to the face information of the at least one object, an object appearing for a first time in the image or an object located at the front of the at least one object in the image as the target object to interact through the interactive interface.

According to the embodiments, the display method 200 may be implemented to capture at least one object present within a field of view of the image sensor 103, i.e., capturing an image of the object in real time using the image sensor 103. Then, a human face in the captured image is detected, where a face detection algorithm may be used to detect the human face in the captured image. At present, common face detection algorithms include AlnnoFace face detection algorithm, cascaded CNN (convolutional neural network) face detection algorithm, OpenCV face detection algorithm, Seetaface face detection algorithm, libfacedetect face detection algorithm, FaceNet face detection algorithm, MTCNN (Multi-task convolutional neural network) face detection algorithm, etc. The embodiments of the present disclosure do not limit the face detection algorithm used, and any suitable method may be used to detect the face.

The display method for the interactive interface according to the embodiments of the present disclosure may be implemented to provide a display of a single-person interaction scene and a display of a multi-person interaction scene. The single-person interaction scene refers to a scene with a single interaction object, in which an interaction is made with the single interaction object. The multi-person interaction scene may refer to a scene with a plurality of interaction objects, in which an interaction object is selected from the plurality of interaction objects for an interaction. Whether a specific interaction is based on the single-person interaction scene or based on the multi-person interaction scene may be pre-selected by setting a system parameter. For example, for a scene with a plurality of interaction objects, the interaction may be set as the multi-person interaction scene.

The display method for the interactive interface according to the embodiments of the present disclosure may be implemented to determine the target object in different ways. According to the embodiments, an object appearing for a first time in the captured image may be determined as the target object to interact through the interactive interface, which is suitable for both the single-person interaction scene and the multi-person interaction scene. According to the embodiments, an object located at the front of a plurality of objects in the captured image may also be determined as the target object to interact through the interactive interface, which is suitable for the multi-person interaction scene in which the plurality of interaction objects appear simultaneously in the captured image. It may be understood that the image sensor 103 may be a depth image sensor, the captured image may be a depth image, and the display method according to the embodiments of the present disclosure may be implemented to determine the object located at the front by identifying a depth information of each object in the captured image.

Next, in step S220, by tracking and detecting the target object, an image of the target object may be acquired in real time, a face information of the target object in the image may be acquired in real time, and the attribute information and the emotion information of the target object may be acquired in real time according to the face information.

After the target object is determined, the target object may be tracked, so as to acquire an emotion value of the target object in real time. Specifically, a face tracking and smoothing algorithm may be used to track and detect the target object. After a face is detected in the image captured by the image sensor 103 and the target object is determined, the display method may be implemented to identify a position of the face of the target object in the image and display an image representing the face of the target object on the interactive interface 101. When the target object moves freely, the image representing the face on the interactive interface may move with a movement of the target object, so as to achieve smooth tracking of the target object. At present, common face tracking and smoothing algorithms include MTCNN algorithm, Laplace algorithm, particle filter algorithm, etc., and a combined technology of Kalman filter and Hungarian algorithm may also be used, which is not limited in the embodiments of the present disclosure.

According to the embodiments, the attribute information of the target object may contain an age and a gender of the target object, but is not limited thereto. A step of acquiring the age and the gender of the target object includes acquiring a face information of the target object by identifying the image containing the face of the target object, and acquiring the age of the target object by using an age estimation algorithm according to the face information. Common age estimation algorithms include SVM (Support Vector Machine), CNN, etc. Further, the gender of the target object may be acquired by using a gender estimation algorithm according to the face information. Common gender estimation algorithms include SVM, CNN, etc. The embodiments of the present disclosure do not limit the age estimation algorithm and the gender estimation algorithm used herein, and any suitable method may be used.

According to the embodiments, the emotion information of the target object may be represented by the emotion value of the target object. A step of acquiring the emotion value of the target object includes acquiring a face information of the target object by identifying the image containing the face of the target object, and acquiring the emotion value of the target object by using an emotion recognition algorithm according to the face information. Common emotion recognition algorithms include KNN (K-Nearest Neighbor) algorithm, SVM algorithm, clustering algorithm, genetic algorithm, PSO (Particle Swarm Optimization) algorithm, CNN algorithm, MTCNN algorithm, etc. The embodiments of the present disclosure do not limit the emotion recognition algorithm used herein, and any suitable method may be used.

According to the embodiments, eight emotions of the target object may be recognized through the emotion recognition algorithm, including neutrality, happiness, surprise, sadness, anger, fear, disgust and contempt, and each emotion corresponds to a emotion value. The emotion of the target object may exhibit a complex state in which various emotions are intertwined. For example, the target object may be in a state of contempt, but an overall emotion may be stable without an emotional fluctuation, that is, the target object is still in a state of neutrality. Therefore, it is required to comprehensively determine an actual emotion category of the target object according to the aforementioned emotion value. Under a normal circumstance, neutrality and surprise may be considered as a neutral emotion, that is, when the target object is in a state of neutrality or surprise, the target object is in a calm state as a whole without a large emotional fluctuation. Sadness, anger, fear, disgust and contempt may be considered as negative emotions, that is, when the target object is in a state of sadness, anger, fear, disgust or contempt, the emotion of the target object is low or has a large negative fluctuation. It may be considered that happiness is a positive emotion. It is easy to understand that when the target object is in a state of happiness, the emotion of the target object has a positive fluctuation or is high.

The emotion recognition algorithm may express the emotion of the target object with different emotion values. In general, the negative emotion such as sadness, anger, fear, disgust and contempt has a low emotion value, the positive emotion such as happiness has a high emotion value, and the neutral emotion such as neutrality and surprise has an emotion value between the emotion value of the positive emotion and the emotion value of the negative emotion. Therefore, the emotion of the target object may be represented by different values.

Next, in step S230, controlling the display of the first object region of the interactive interface according to the attribute information and the emotion information of the target object includes determining a display image for the target object on the interactive interface according to the attribute information of the target object. According to the embodiments, the interactive interface 101 may be divided into different object regions, and the display method according to the embodiments of the present disclosure may be implemented to control and display the different object regions respectively, so as to increase a display flexibility.

Figure 3A:
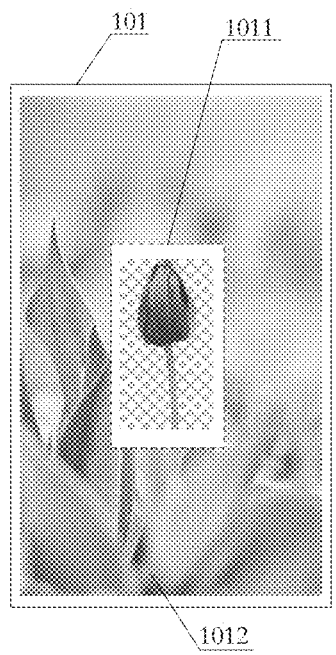
FIG. 3A and FIG. 3B show a display example of an interactive interface according to the embodiments of the present disclosure.
Figure 3B:
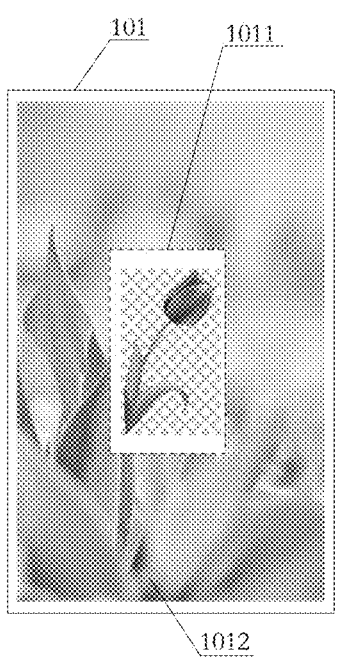

FIG. 3A and FIG. 3B show a display example of the interactive interface according to the embodiments of the present disclosure. As shown in FIG. 3A and FIG. 3B, the interactive interface 101 includes a first object region 1011 and a second object region 1012. The first object region 1011 may be a region configured to display the target object, which presents the display image for the target object on the interactive interface 101. The second object region 1012 may be a region configured to display other content than the display image for the target object, such as a background display region on the interactive interface 101. A position of the first object region 1011 on the interactive interface 101 may be changed, and the first object region 1011 may be moved on the interactive interface 101, so as to provide a dynamic display effect.

Determining the display image for the target object on the interactive interface according to the attribute information of the target object may include determining the display image for the target object in the first object region of the display interface according to the age and the gender of the target object. As shown in FIG. 3A and FIG. 3B, a tulip shown is the display image for representing the target object determined according to the age and the gender of the target object.

Next, in step S230, controlling the display of the first object region of the interactive interface according to the attribute information and the emotion information of the target object further includes varying the display image in the first object region according to the emotion information of the target object. According to the embodiments, varying the display image in the first object region according to the emotional information of the target object may include determining an emotional characteristic value of the target object according to the emotion value of the target object and controlling the display of the display image according to a comparison result between the emotional characteristic value of the target object and an emotion threshold. When the emotional characteristic value is less than a first emotion threshold, the display image for the target object is displayed in a first display mode as the emotional characteristic value decreases. When the emotional characteristic value is greater than or equal to the first emotion threshold and less than or equal to a second emotion threshold, the display image for the target object is maintained. When the emotional characteristic value is greater than the second emotion threshold, the display image for the target object is displayed in a second display mode as the emotional characteristic value increases.

Due to a complexity of the actual emotional state of the object, a comprehensive emotional state of the target object is indicated by the recognized emotion information (emotion value) of the target object. The first emotion threshold and the second emotion threshold are predetermined thresholds according to the emotional state of the object. A value of the first emotion threshold is less than a value of the second emotion threshold, and the value of the first emotion threshold and the value of the second emotion threshold may be adjusted according to the actual situation of different objects. The first display mode and the second display mode may be associated with the display image and may be determined in combination with the specific display image. For example, when the display image is a tulip as shown in FIG. 3A and FIG. 3B, the first display mode may be that the tulip gradually closes from an open state (as shown in FIG. 3A), and the second display mode may be that the tulip gradually blooms from an open or closed state (as shown in FIG. 3B). The gradual closing of the tulip from the open state may indicate that the target object is in a negative emotional state and is unwilling to communicate. The gradual blooming of the tulip from the open or closed state indicates that the target person is in a positive emotional state and is willing to communicate. In addition, according to the embodiments, the display of the display image may be adjusted according to a change in the emotional characteristic value, and a change in the emotion of the target object may be presented through the varying of the display image. For example, when the tulip gradually closes from the open state, it indicates that the emotion of the target object is becoming lower and lower, while when the tulip gradually blooms from the open or closed state, it indicates that the emotion of the target is gradually rising.

According to the embodiments of the present disclosure, by controlling the display of the display image in the first display mode and the second display mode respectively, not only the emotional state of the target object may be expressed more accurately and the change in the emotion of the target object may be exhibited, which is beneficial to monitor the emotional state of the target object in real time, but also the interest of the display may be increased, which is beneficial to arouse the emotion of the target object, so as to perform an auxiliary treatment on the target object.

It is easy to understand that the emotion threshold is not limited to the first emotion threshold and the second emotion threshold, and the display mode is not limited to the first display mode and the second display mode. More display modes may be defined according to the emotional state of the target object to provide richer information about the target object. For example, in a case that the emotional characteristic value is less than the first emotion threshold and gradually increases but does not reach the first emotion threshold, the display image for the target object (the tulip in FIG. 3A is still illustrated by way of example) may be displayed in a mode such that the tulip in the closed state exhibits a change towards the open state. As shown in FIG. 3A, the tulip may have a small closed bud at the beginning, and as the emotional characteristic value increases, the closed bud is not yet open but becomes larger and tends to open. Similarly, in a case that the emotional characteristic value is greater than the second emotion threshold and gradually decreases but does not reach the second emotion threshold, the display image for the target object (the tulip in FIG. 3B is still illustrated by way of example) may be displayed in a mode such that the tulip in the open state exhibits a change towards the closed state. As shown in FIG. 3B, the tulip may have a large open flower at the beginning, and as the emotional characteristic value decreases, the large flower becomes smaller but is still open.

The embodiments of the present disclosure provide an emotion recognition-based display method for an interactive interface. The display method may be implemented to recognize the emotion of the target object in real time and dynamically adjust the display of the interactive interface. When a face is detected in the image, the corresponding display image may be displayed. The target object may be classified using the age estimation algorithm and the gender estimation algorithm, so as to display different images. By displaying an appropriate picture, the interest of the display is increased, the resistance of the target object to the interaction through the interactive interface may be alleviated and eliminated, and the emotional state information of the target object may be acquired more accurately, which is conducive to the assessment and treatment of the emotional state of the target object.

Figure 4:
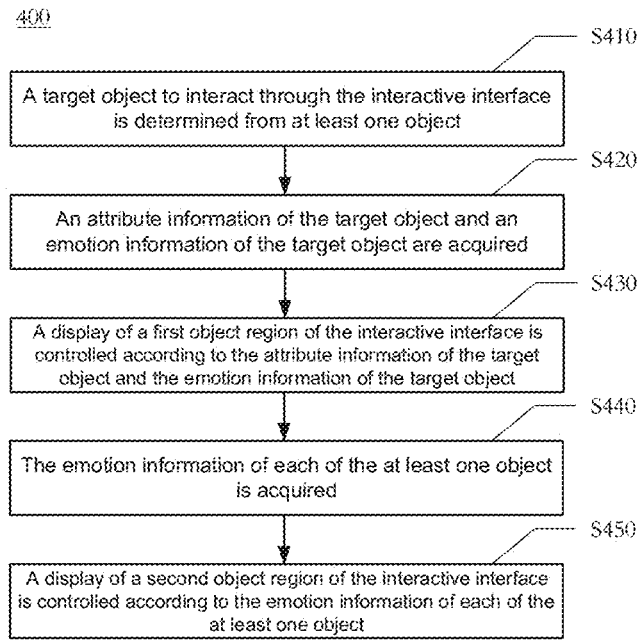
FIG. 4 shows another flowchart of a display method for an interactive interface according to the embodiments of the present disclosure.

FIG. 4 shows another flowchart of a display method for an interactive interface according to the embodiments of the present disclosure. As shown in FIG. 4, a display method 400 may include the following steps.

In step S410, a target object to interact through the interactive interface is determined from at least one object.

In step S420, an attribute information of the target object and an emotion information of the target object are acquired.

In step S430, a display of a first object region of the interactive interface is controlled according to the attribute information of the target object and the emotion information of the target object.

In step S440, the emotion information of each of the at least one object is acquired.

In step S450, a display of a second object region of the interactive interface is controlled according to the emotion information of each of the at least one object.

The operations performed in step S410, step S420 and step S430 are the same as those performed in step S210, step S220 and step S230 in the display method 200, which will not be described in detail here. In addition, step S440 and step S450 may be performed in parallel with step S420 and step S430. Step S440 and step S450 will be described in detail below with reference to the embodiments.

According to an embodiment, controlling the display of the second object region of the interactive interface according to the emotion information of each of the at least one objects specifically includes: determining an emotional characteristic value of each of the at least one object according to the emotion value of each of the at least one object; acquiring an average value of the emotional characteristic value according to the emotional characteristic value of each of the at least one object; displaying a background pattern in the second object region in a third mode as the average value of the emotional characteristic value decreases, in response to the average value of the emotional characteristic value being less than a first average emotion value threshold; maintaining the background pattern in the second object region in response to the average value of the emotional characteristic value being greater than or equal to the first average emotion value threshold and less than or equal to a second average emotion value threshold; and displaying the background pattern in the second object region in a fourth mode as the average value of the emotional characteristic value increases, in response to the average value of the emotional characteristic value being greater than the second average emotion value threshold.

Figure 5A:
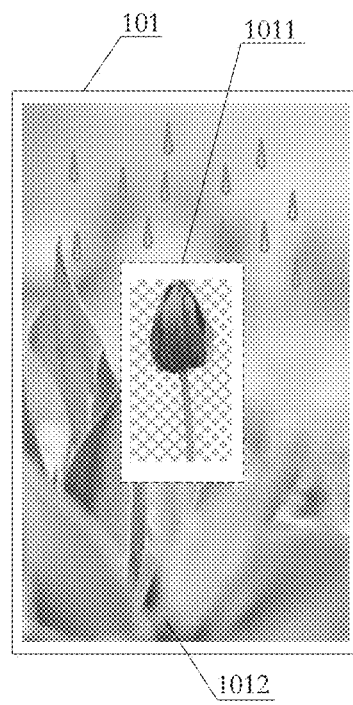
FIG. 5A and FIG. 5B show another display example of an interactive interface according to the embodiments of the present disclosure.
Figure 5B:
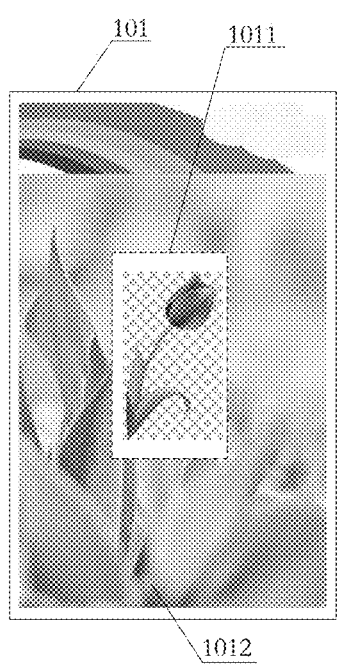

In this embodiment, the average value of the emotional characteristic value is a value obtained by averaging the emotional characteristic value of each object including the target object in the acquired image, which may roughly indicate an overall emotional state of all objects in the image. FIG. 5A and FIG. 5B show another display example of the interactive interface according to the embodiments of the present disclosure. As shown in FIG. 5A, when the average value of the emotional characteristic value is less than a first average emotion value threshold, it indicates that the overall emotional state of all objects in the image is low, and the whole is in a negative emotion, so that an element such as wind or rain may be added to the second object region (e.g., a background image). As shown in FIG. 5B, when the average value of the emotional characteristic value is greater than a second average emotion value threshold, it indicates that the overall emotional state of all objects in the image is positive, and the whole is in a positive emotion, so that an element such as sunlight or rainbow may be added to the second object region (e.g., the background image).

By adjusting the display of the second object region according to the average value of the emotional characteristic values of the crowd, the emotion information of other people in the scene where the target object is located may be better shown. Since human emotions are easily affected by an outside world, according to the embodiments of the present disclosure, the emotion of the target object may be monitored more comprehensively, and diversified information may be provided for the assessment and treatment of the target object.

It is easy to understand that the average emotion value threshold is not limited to the first average emotion value threshold and the second average emotion value threshold, and the display mode is not limited to the third display mode and the fourth display mode. More display modes may be defined according to the emotional state of the crow in which the target object is located, so as to provide richer information about the target object.

In addition, in a case of the single-person interaction, the display of the second object region may also be adjusted according to the emotional characteristic value of the target object. In this case, the emotional characteristic value of the target object is used as the average value of the emotional characteristic value.

Figure 6:
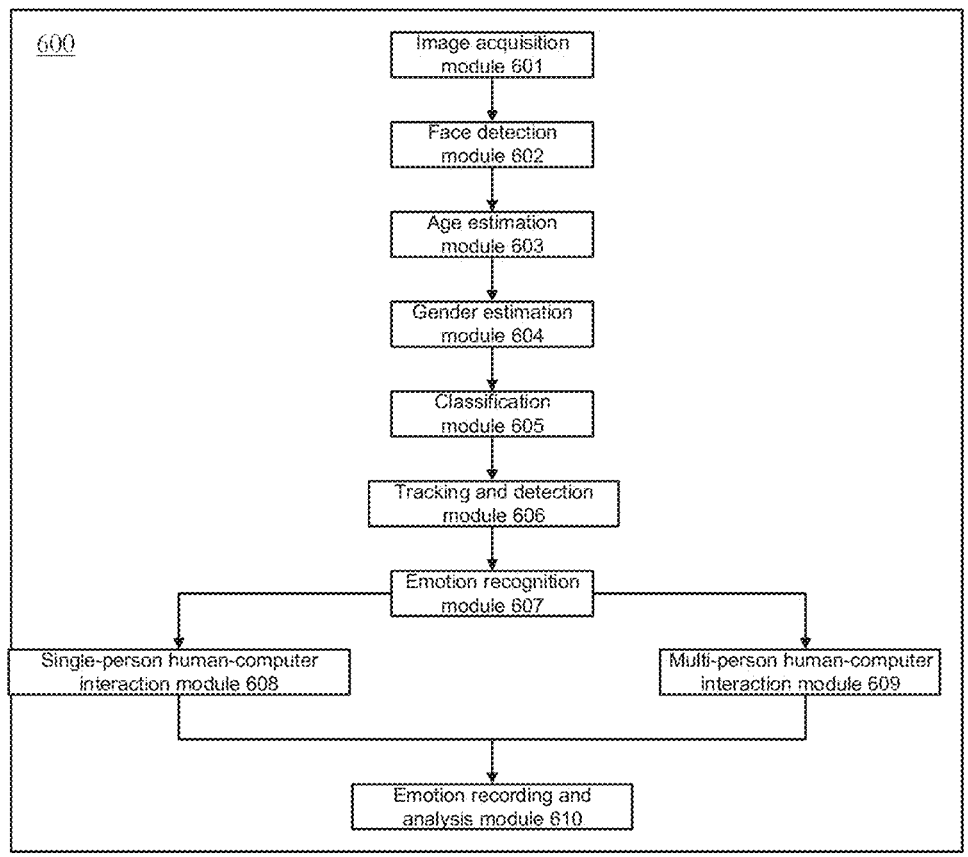
FIG. 6 shows an example of a display device for an interactive interface according to the embodiments of the present disclosure.

FIG. 6 shows an example of a display device for an interactive interface according to the embodiments of the present disclosure. As shown in FIG. 6, a display device 600 for an interactive interface includes an image acquisition module 601, a face detection module 602, an age estimation module 603, a gender estimation module 604, a classification module 605, a tracking and detection module 606, an emotion recognition module 607, a single-person human-computer interaction module 608, a multi-person human-computer interaction module 609 and an emotion recording and analysis module 610. The image acquisition module 601 is configured to receive an image about at least one object captured by an image sensor. The face detection module 602 is configured to identify the image to acquire a face information of the at least one object in the image, and determine the target object. The age estimation module 603 is configured to acquire an age of the target object by using an age estimation algorithm according to the face information of the target object in the face information of the at least one object. The gender estimation module 604 is configured to acquire a gender of the target object by using a gender estimation algorithm according to the face information of the target object in the face information of the at least one object. The classification module 605 is configured to determine a display image for the target object according to the estimated age information and gender information. In this example, the display image for the target object may be determined according to the information shown in Table 1. For example, when the gender of the target object is female and the age is between 30-50 years old, a tulip may be used as the display image for the target object.

TABLE 1

| Gender | Age | Image | Gender | Age | Image |
|---|---|---|---|---|---|
| Male | 0-15 | Grass | Female | 0-15 | Bud |
| Male | 15-30 | Small tree | Female | 15-30 | Rose |
| Male | 30-50 | Big tree | Female | 30-50 | Tulip |
| Male | 50-65 | Eagle | Female | 50-65 | Rosebush |
| Male | 65~ | Seagull | Female | 65~ | Peony |

The tracking and detection module 606 is configured to track and detect the target object using a face tracking and smoothing algorithm, and identify a position of the face of the target object on the image, so as to display an image representing the face of the target object on the interactive interface. The emotion recognition module 607 is configured to acquire the face information from the tracking and detection module 606 in real time, and acquire an emotion value of the target object according to an emotion recognition algorithm.

The single-person human-computer interaction module 608 may provide an interactive interface under the single-person scene, and is configured to perform the following processing according to the emotion value of the target object recognized by the emotion recognition module 607.

Emotion values of eight emotions of the target object may be represented by a1, a2, a3, a4, a5, a6, a7 and a8 respectively. A fitting is performed on the emotion values according to Expression (1), so as to obtain the emotion charac-teristic value of the target object, where all values in the fitting process are rounded up.

$$w_1 = a_2, w_2 = a_8 + 2a_4 + a_5 + a_6 + a_7 - a_3$$

if $w_1 > w_2$, then $W_{target} = w_1$ $w_1 = w_2$, then $W_{target} = k$ $w_1 < w_2$, then $W_{target} = w_2$      Expression (1)

where $w_1$ and $w_2$ are preset fitting variables, k is a preset constant, and $W_{target}$ represents the emotional characteristic value of the target object.

Further, the first emotion threshold is set as $k_1=30$, and the second emotion threshold is set as $k_2=80$, then the preset constant may be set as $k=50$, so that the emotion value of the target object is between $k_1$ and $k_2$ when $w_1=w_2$.

The single-person human-computer interaction module 608 may further control the display of the first object region according to a determination of the following condition.

When $W_{target} < k_1$, the tulip gradually closes as the value of $W_{target}$ decreases.

When $k_1 \leq W_{target} \leq k_2$, the tulip is maintained in a normal open state and does not vary.

When $W_{target} > k_2$, the tulip gradually exhibits a blooming state with the increase of the value of $W_{target}$.

The multi-person human-computer interaction module 609 may provide an interactive interface under the multi-person scene. A process of the multi-person human-computer interaction module 609 determining the emotional characteristic value of the target object and controlling the display of the display image for the target object according to the emotional characteristic value of the target object is the same as that of the single-person human-computer interaction module. 608, which will not be repeated here.

In addition, the multi-person human-computer interaction module 609 is further configured to perform the following processing according to the emotion value of each object recognized by the emotion recognition module 607.

The emotional characteristic values of n objects in the captured image are represented by $W_1, W_2, W_3, \ldots, W_n$ respectively, then an average value of the emotional characteristic values of all objects in the entire scene may be represented by Expression (2).

$$W_{average} = \Sigma_{i=1}^{n} W_i / n$$      Expression (2)

Further, a first average emotion value threshold is represented by $h_1$, which may be 30, and a second average emotion value threshold is represented by $h_2$, which may be 80.

The multi-person human-computer interaction module 609 may further control the display of the second object region according to a determination of the following condition.

When $W_{average} < h_1$, an element such as wind or rain may be added to the background of the display screen.

When $h_1 \leq W_{average} \leq h_2$, the background of the display screen is kept unchanged.

When $W_{average} > h_2$, an element such as sunlight or rainbow may be added to the background of the display screen.

The emotion recording and analysis module 610 is configured to record the basic information and the emotional state information in the monitoring process of each target object.

Figure 7:
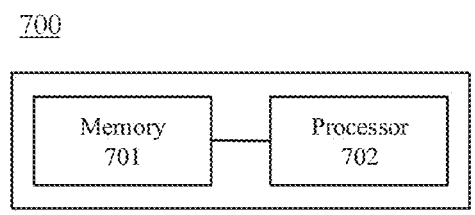
FIG. 7 shows another example of a display device for an interactive interface according to the embodiments of the present disclosure.

FIG. 7 shows another example of a display device for an interactive interface according to the embodiments of the present disclosure. As shown in FIG. 7, a display device 700 for an interactive interface includes a memory 701 and a processor 702. The memory 701 is configured to store program instructions. The processor 702 is configured to execute the program instructions to: determine, from at least one object, a target object to interact through the interactive interface, acquire an attribute information of the target object and an emotion information of the target object, and control a display of a first object region of the interactive interface according to the attribute information of the target object and the emotion information of the target object. In addition, the processor 702 is further configured to acquire an emotion information of each of the at least one object, and control a display of a second object region of the interactive interface according to the emotion information of each of the at least one object.

Moreover, although various components are shown in the various block diagrams above, those skilled in the art may understand that the embodiments of the present disclosure may be implemented in the absence of one or more components or in a combination of some components.

In addition, although the various steps are described above in the order shown in the figures, those skilled in the art may understand that the embodiments of the present disclosure may be implemented without one or more of the above-described steps.

It may be understood from the above contents that an electronic component of one or more systems or devices may include, but is not limited to, at least one processing unit, a memory, and a communication bus or communication device that couples various components including the memory to the processing unit. The system or device may include or have access to various device-readable mediums. The system memory may include a device-readable storage medium in a form of volatile and/or nonvolatile memory (e.g., read only memory (ROM) and/or random access memory (RAM)). By way of example and not limitation, the system memory may further include an operating system, an application, other program modules and program data.

An embodiment may be implemented as a system, a method or a program product. Therefore, an embodiment may be in the form of an entirely hardware embodiment or an embodiment including software (including firmware, resident software, microcode, etc.), which may be collectively referred to herein as a "circuit," "module," or "system." Furthermore, an embodiment may be in a form of a program product embodied in at least one device-readable medium having device-readable program code embodied thereon.

A combination of device-readable storage mediums may be used. In the context of this document, the device-readable storage medium ("storage medium") may be any tangible, non-signal medium that may contain or store a program composed of program codes configured for use by or in connection with an instruction execution system, apparatus or device. For the purpose of the present disclosure, the storage medium or device should be construed as non-transitory, that is, not including a signal or a propagation medium.

The present disclosure has been presented for a purpose of illustration and description, but is not intended to be exhaustive or limiting. Various modifications and variations will be apparent to those of ordinary skilled in the art. The embodiments may be chosen and described in order to explain the principles and practical application, and to enable those of ordinary skilled in the art to understand various embodiments of the present disclosure with various modifications suitable for the intended specific use.

What is claimed is:

1. A display method for an interactive interface, comprising:

determining, from at least one object, a target object to interact through the interactive interface;

acquiring an attribute information of the target object and an emotion information of the target object; and controlling a display of a first object region of the interactive interface according to the attribute information of the target object and the emotion information of the target object, wherein the controlling a display of a first object region of the interactive interface according to the attribute information of the target object and the emotion information of the target object comprises:

determining a display image for the target object in the first object region of the interactive interface according to the attribute information of the target object; and varying the display image in the first object region according to the emotion information of the target object, wherein the emotion information contains an emotion value, and the varying the display image in the first object region according to the emotion information of the target object comprises:

determining an emotional characteristic value of the target object according to the emotion value of the target object;

displaying the display image in a first display mode as the emotion characteristic value decreases, in response to the emotion characteristic value being less than a first emotion threshold;

maintaining the display image in response to the emotional characteristic value being greater than or equal to the first emotion threshold and less than or equal to a second emotion threshold; and displaying the display image in a second display mode as the emotional characteristic value increases, in response to the emotional characteristic value being greater than the second emotion threshold.

2. The display method of claim 1, wherein the determining, from at least one object, a target object to interact through the interactive interface comprises:

tracking and detecting the at least one object to acquire an image about the at least one object;

identifying the image to acquire a face information of the at least one object in the image; and determining, according to the face information of the at least one object, an object appearing for a first time in the image or an object located at the front of the at least one object in the image as the target object to interact through the interactive interface.

3. The display method of claim 2, wherein the attribute information contains an age and a gender, and the acquiring an attribute information of the target object comprises:

acquiring the age of the target object by using an age estimation algorithm according to a face information of the target object in the face information of the at least one object; and acquiring the gender of the target object by using a gender estimation algorithm according to the face information of the target object in the face information of the at least one object.

4. The display method of claim 2, wherein the emotion information contains an emotion value, and the acquiring an emotion information of the target object comprises:

acquiring the emotion value of the target object by using an emotion recognition algorithm according to the face information of the target object in the face information of the at least one object.

5. The display method of claim 4, wherein the emotion recognition algorithm comprises one of a K-nearest neighbor algorithm, a support vector machine algorithm, a clustering algorithm, a genetic algorithm, a particle swarm optimization algorithm, a convolutional neural network algorithm and a multi-task convolutional neural network algorithm.

6. The display method of claim 1, further comprising:
acquiring an emotion information of each of the at least one object; and
controlling a display of a second object region of the interactive interface according to the emotion information of each of the at least one object.

7. The display method of claim 6, wherein the emotion information contains an emotion value, and the controlling a display of a second object region of the interactive interface according to the emotion information of each of the at least one object comprises:
determining an emotional characteristic value of each of the at least one object according to the emotion value of each of the at least one object;
acquiring an average value of the emotional characteristic value according to the emotional characteristic value of each of the at least one object;
displaying a background pattern in the second object region in a third mode as the average value of the emotional characteristic value decreases, in response to the average value of the emotional characteristic value being less than a first average emotion value threshold;
maintaining the background pattern in the second object region in response to the average value of the emotional characteristic value being greater than or equal to the first average emotion value threshold and less than or equal to a second average emotion value threshold; and
displaying the background pattern in the second object region in a fourth mode as the average value of the emotional characteristic value increases, in response to the average value of the emotional characteristic value being greater than the second average emotion value threshold.

8. A display device for an interactive interface, comprising:
a memory configured to store program instructions; and
a processor configured to execute the program instructions to:
determine, from at least one object, a target object to interact through the interactive interface;
acquire an attribute information of the target object and an emotion information of the target object; and
control a display of a first object region of the interactive interface according to the attribute information of the target object and the emotion information of the target object,
wherein the processor is further configured to:
determine a display image for the target object in the first object region of the interactive interface according to the attribute information of the target object; and
vary the display image in the first object region according to the emotion information of the target object,
wherein the emotion information contains an emotion value, and the processor is further configured to:
determine an emotional characteristic value of the target object according to the emotion value of the target object;
display the display image in a first display mode as the emotion characteristic value decreases, in response to the emotion characteristic value being less than a first emotion threshold;
maintain the display image in response to the emotional characteristic value being greater than or equal to the first emotion threshold and less than or equal to a second emotion threshold; and
display the display image in a second display mode as the emotional characteristic value increases, in response to the emotional characteristic value being greater than the second emotion threshold.

9. The display device of claim 8, wherein the processor is further configured to:
acquire an emotion information of each of the at least one object; and
control a display of a second object region of the interactive interface according to the emotion information of each of the at least one object.

10. The display device of claim 9, wherein the emotion information contains an emotion value, and the processor is further configured to:
determine an emotional characteristic value of each of the at least one object according to the emotion value of each of the at least one object;
acquire an average value of the emotional characteristic value according to the emotional characteristic value of each of the at least one object;
display a background pattern in the second object region in a third mode as the average value of the emotional characteristic value decreases, in response to the average value of the emotional characteristic value being less than a first average emotion value threshold;
maintain the background pattern in the second object region in response to the average value of the emotional characteristic value being greater than or equal to the first average emotion value threshold and less than or equal to a second average emotion value threshold; and
display the background pattern in the second object region in a fourth mode as the average value of the emotional characteristic value increases, in response to the average value of the emotional characteristic value being greater than the second average emotion value threshold.

11. The display device of claim 8, wherein the processor is further configured to:
track and detecting the at least one object to acquire an image about the at least one object;
identify the image to acquire a face information of the at least one object in the image; and
determine, according to the face information of the at least one object, an object appearing for a first time in the image or an object located at the front of the at least one object in the image as the target object to interact through the interactive interface.

12. The display device of claim 11, wherein the attribute information contains an age and a gender, and the processor is further configured to:
acquire the age of the target object by using an age estimation algorithm according to a face information of the target object in the face information of the at least one object; and acquire the gender of the target object by using a gender estimation algorithm according to the face information of the target object in the face information of the at least one object.

13. The display device of claim 11, wherein the emotion information contains an emotion value, and the processor is further configured to:
acquire the emotion value of the target object by using an emotion recognition algorithm according to the face information of the target object in the face information of the at least one object.

14. The display device of claim 13, wherein the emotion recognition algorithm comprises one of a K-nearest neighbor algorithm, a support vector machine algorithm, a clustering algorithm, a genetic algorithm, a particle swarm optimization algorithm, a convolutional neural network algorithm and a multi-task convolutional neural network algorithm.

15. A non-transitory computer-readable storage medium having executable instructions stored thereon, wherein the instructions, when executed by a processor, cause the processor to perform a display method for an interactive interface, comprising:
determining, from at least one object, a target object to interact through the interactive interface;
acquiring an attribute information of the target object and an emotion information of the target object; and
controlling a display of a first object region of the interactive interface according to the attribute information of the target object and the emotion information of the target object,
wherein the controlling a display of a first object region of the interactive interface according to the attribute information of the target object and the emotion information of the target object comprises:
determining a display image for the target object in the first object region of the interactive interface according to the attribute information of the target object; and
varying the display image in the first object region according to the emotion information of the target object,
wherein the emotion information contains an emotion value, and the varying the display image in the first object region according to the emotion information of the target object comprises:
determining an emotional characteristic value of the target object according to the emotion value of the target object;
displaying the display image in a first display mode as the emotion characteristic value decreases, in response to the emotion characteristic value being less than a first emotion threshold;
maintaining the display image in response to the emotional characteristic value being greater than or equal to the first emotion threshold and less than or equal to a second emotion threshold; and
displaying the display image in a second display mode as the emotional characteristic value increases, in response to the emotional characteristic value being greater than the second emotion threshold.

\* \* \* \* \*